(12) United States Patent
Abdel-Hadi et al.

(10) Patent No.: US 7,055,374 B2
(45) Date of Patent: Jun. 6, 2006

(54) SYSTEM FOR CHARACTERIZING BULK MECHANICAL PROPERTIES OF AERATED MATERIALS

(75) Inventors: Ali Ismail Abdel-Hadi, Gainesville, FL (US); Nicolaie D. Cristescu, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 218 days.

(21) Appl. No.: 10/779,509

(22) Filed: Feb. 13, 2004

(65) Prior Publication Data

US 2004/0194543 A1     Oct. 7, 2004

Related U.S. Application Data

(60) Provisional application No. 60/447,396, filed on Feb. 14, 2003.

(51) Int. Cl.
*G01N 15/08* (2006.01)
(52) U.S. Cl. .......................................................... 73/38
(58) Field of Classification Search ...................... 73/38
See application file for complete search history.

(56) References Cited

U.S. PATENT DOCUMENTS

| | | | |
|---|---|---|---|
| 3,616,685 A | * | 11/1971 | Strom ............................ 73/84 |
| 3,788,125 A | * | 1/1974 | Kirschstein et al. ........ 73/32 R |
| 3,839,899 A | | 10/1974 | McMillen |
| 4,561,289 A | | 12/1985 | Jones |
| 4,599,891 A | | 7/1986 | Brauer et al. |
| 4,753,107 A | | 6/1988 | Reed et al. |
| 4,956,993 A | * | 9/1990 | Mehler .......................... 73/38 |
| 5,325,723 A | | 7/1994 | Meadows et al. |
| 6,185,985 B1 | | 2/2001 | Fleury et al. |
| 6,935,159 B1 | * | 8/2005 | Knight et al. ................... 73/38 |

FOREIGN PATENT DOCUMENTS

GB          2128758 A   *   5/1984

* cited by examiner

*Primary Examiner*—Hezron Williams
*Assistant Examiner*—John Fitzgerald
(74) *Attorney, Agent, or Firm*—Akerman Senterfitt

(57) ABSTRACT

A device for determining physical properties of aerated particulate materials. The device may be formed from an inner container positioned in an outer container, wherein the inner container is adapted to hold a particulate material. An air source is in fluid communication with the inner container for passing air through the inner container. A load application device may extend into the inner container for applying an axial load to a particulate material while air is flowing through the particulate material. The device may include an environmental chamber for controlling humidity and temperature of the air being passed through the particulate material. The device may also include numerous sensors for measuring temperature, pressure, changes in volume, humidity, and other parameters. The sensors may be monitored by a storage device, such as a computer.

28 Claims, 5 Drawing Sheets

SYSTEM FOR CHARACTERIZING BULK MECHANICAL PROPERTIES OF AERATED MATERIALS

CROSS-REFERENCE TO RELATED APPLICATION

This application claims the benefit of U.S. Provisional Application No. 60/447,396, filed Feb. 14, 2003.

FIELD OF THE INVENTION

The invention is directed generally to testing equipment, and more particularly, to equipment for testing aerated particulate materials.

BACKGROUND

Particulate materials, such as powders, grains, seeds, chips, and the like, have been transported in manufacturing processes in numerous manners. For instance, particulate materials have been transported using conveyor belts, containers, and other devices. Unlike some bulk materials, particulate materials can be transported through conduits. Typically, particulate materials are transported through pipes using augers and gravity feed systems. Conveying systems using augers have been successful; however, augers can be expensive to acquire, operate, and maintain. In addition, augers often add undue complexity to a conveying system needing only to move a particulate material between two locations.

Gravity feed systems have also been successful in transporting particulate materials; however, gravity systems are limited to transporting materials from a first location that is higher than a second location. Without such a configuration, gravity systems are inoperable. In addition, gravity systems are susceptible to failure if moisture is present in the particulate material causing the particulate material to agglomerate and form a mass of varying size and shape that prevents or restricts flow of the particulate material through a system.

The disadvantages of the auger and gravity feed systems have been overcome, in part, by using aeration to assist in transporting particulate material through conduits. Aeration has proven useful in counteracting the effects of moisture in systems transporting particulate material. Often times, existing systems are retrofitted to incorporate aeration systems to increase the systems' ability to transport particulate materials. These systems are often retrofitted before a complete understanding of the characteristics of the particulate material being transported are known. Thus, aeration is often included in these systems without knowing what rate of air flow added to the particulate material is most efficient. Without such an understanding of how a particular type of particulate material and a particular sample reacts under aerated conditions, designing an efficient system is less likely. Thus, a need exists for a system for characterizing a particulate material in an aerated state.

SUMMARY OF THE INVENTION

The invention is directed to a particulate measuring system for measuring one or more parameters of a particulate material with or without aeration. The system may include a test chamber for containing a particulate material and applying an axial load to a particulate material. The test chamber may include an inner container configured to contain a particulate material. The inner container may include one or more inlets and outlets for receiving and expelling one or more gases respectively. In one embodiment, a filter is positioned in the inner container so that fluids received from the inlet first pass through the filter before being released into the inner container. The filter evenly disperses the fluids into the inner container. A second filter may be used to prevent a portion or all of the sample of particulate material from passing through the outlet. A load application device may be coupled to a top end of the inner container for applying an axial load to a particulate material contained in the inner container. The load application device may be coupled to a device capable of applying a load to a shaft of the load application device and displaying the amount of load applied. The test chamber may also include an outer container sized to contain the inner container and form an outside wall of the test chamber. The outer container may have any size and shape and is configured to contain a fluid used to determine changes in volume of the inner chamber.

The system may also include a volume change sensor for determining the volumetric change in the inner container when a load is applied to a particulate material. The particulate measuring system may also include a computer for displaying the results of a test and performing any desired calculations, comparisons, or other manipulations of the test results. The particulate measuring system may also have an environmental chamber for controlling various parameters, such as, but not limited to, temperature and humidity of the gases passed through a sample of particulate material, during the testing process.

The particulate measuring system may be capable of quantifying parameters of particulate material in an aerated state that are useful in designing systems using aeration to transport materials in, for instance, manufacturing processes. The particulate measuring system may be able to determine the total axial load a particulate material can withstand before failure at different flow rates of a gas through the particulate material. The particulate measuring system may be able to measure the pressure differential across a particulate material when the particulate material is subjected to different axial loads. The particulate measuring system may also be able to measure the volumetric change of a particulate material as an axial load is applied to a particulate material using the load application device by sensing changes in volume of fluids contained in the space between the outer container and the inner container. The particulate measuring system may measure the pressure of a fluid in the outer container surrounding the sample of particulate material. In addition, the particulate measuring system may measure the amount and rate of gas flow through the sample of particulate material. This measurement may be used to determine the degree of aeration and whether the particulate material has been fluidized. The measurements capable of being made by the particulate measuring system are set forth as examples and not as limitations. The particulate measuring system may measure other parameters as well.

BRIEF DESCRIPTION OF THE DRAWINGS

The accompanying drawings, which are incorporated in and form a part of the specification, illustrate preferred embodiments of the presently disclosed invention(s) and, together with the description, disclose the principles of the invention(s). These several illustrative figures include the following.

DETAILED DESCRIPTION OF THE INVENTION

This invention is directed to a particulate measuring system 10, as shown in FIGS. 1–6, for measuring numerous characteristics of particulate materials. Particulate measuring system 10 may measure a sample of particulate material while the particulate material is aerated or not aerated. Particulate measuring system 10 may determine physical properties of a particulate material while in low confining pressures. An aerated particulate material is a particulate material having molecules of a gas mixed with the particles of the material. Particulate measuring system 10 is generally composed of a chamber for containing a sample of a particulate material, applying an axial load to the sample, and measuring various characteristics of the particulate material while the particulate material is under a load.

Figure 3:
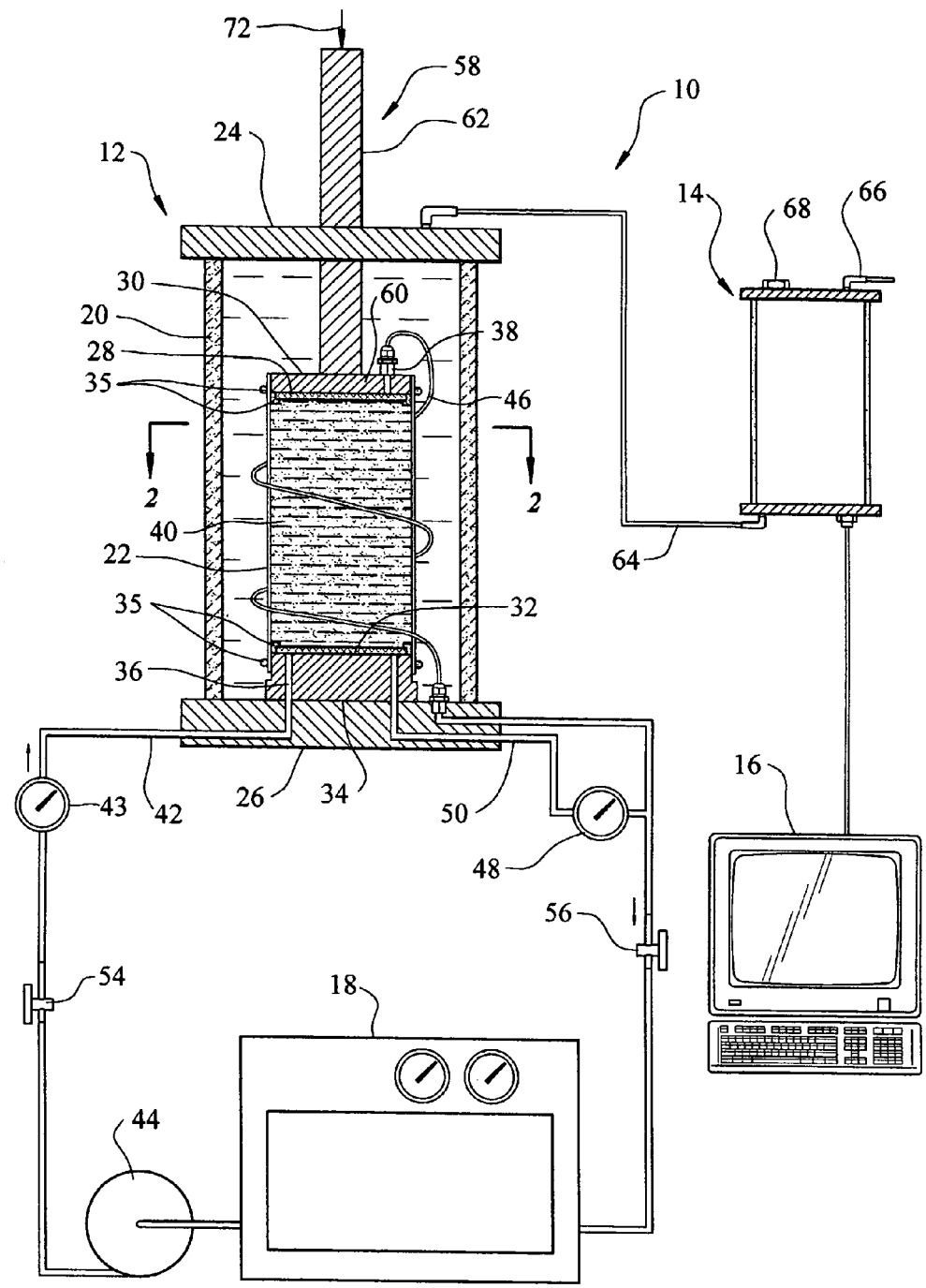
FIG. 3 is schematic diagram of another embodiment of this invention including an environmental chamber.

FIGS. 1–6 depict particulate measuring system 10 for measuring and quantifying properties associated with aerated or non-aerated particulate material, or both. This system may have numerous configurations. Generally, the particulate measuring system 10 may include a test chamber 12 for containing a sample of a particulate material. The test chamber 12 may be a triaxial cell that completely encompasses a sample of particulate material. The test chamber enables separate and independent fluid flow into and out of the sample so that two-phase gas-solid effects on a material may be identified. The sample may be aerated or not and tested to quantify numerous characteristics of the material. Test chamber 12 may be coupled to a volume change sensor 14 for determining the volumetric change of a portion of test chamber 12. A computer 16 may be included in particulate measuring system 10 for displaying the results of a test and performing any desired calculations, comparisons, or other manipulations of the test results. A chamber 18, which may be referred to as an environmental chamber and is shown in FIG. 3, may also be included in particulate measuring system 10 for controlling various parameters, such as humidity and temperature, during the testing process.

Figures 1, 2:
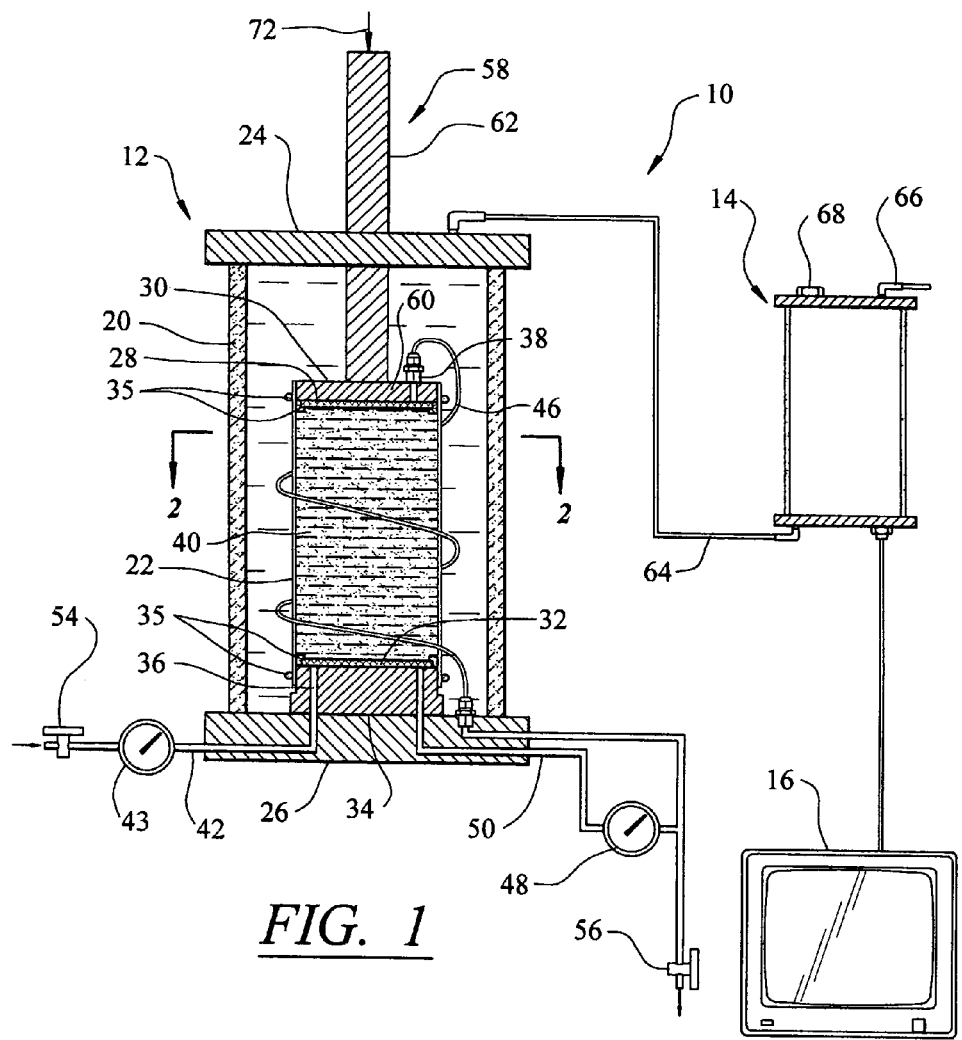
FIG. 1 is a schematic diagram of a particulate measuring system of this invention, whereby the volume change sensor and the test chamber are shown as section views.
FIG. 2 is a cross-sectional view of the test chamber taken at section line 2—2 in FIG. 1 and shown as a complete cylinder.

Test chamber 12 may be formed from an outer container 20 and an inner container 22 that is smaller than outer container 20 and configured to fit within the outer container 20. Outer and inner containers, 20 and 22 respectively, may have cylindrical outer walls, as shown in FIG. 2. However, other embodiments may have outer walls with different shapes. Outer container 20 may have a top end 24 and a bottom end 26 coupled to outer container 20 so that a fluid may not undesirably escape from outer container 20. In one embodiment, test chamber 12 is formed from inner container 22 and does not include outer chamber 20.

Inner container 22 may have an outer wall formed from a membrane, an outlet filter 28 on top end 30 and an inlet filter 32 bottom end 34 of inner container 22. The membrane may be sized to prevent all particles from passing through the membrane or sized to prevent some, but not all, of the particles from passing through the membrane. The membrane may also be formed of numerous materials, such as, but not limited to, latex and other materials. In one embodiment, inner container 22 may be generally cylindrically shaped with a diameter of about three inches and may have a height of about six inches. However, the membrane is not limited to this size but may have other sizes as well. O-rings 35, or other sealing devices, such as, but not limited to, adhesives and the like, may be used to seal outlet filter 28 and inlet filter 32 to inner container 22.

Inner container 22 may include one or more inlets 36 for admitting a fluid, such as a gas, into inner container 22. In one embodiment, inlet 36 may be positioned in bottom end 26 of outer container 22 and may be coupled to inlet filter 32. During use, inlet filter 32 may diffuse a fluid flowing through inlet 36 into inner container 22 and cause the fluid to be dispersed evenly, or relatively evenly, into inner container 22.

Inner container 22 may also include one or more outlets 38 for releasing a fluid from inner container 22. In one embodiment, outlet 38 may be mounted to top end 30 of inner container 22. Outlet 38 may also be coupled to outlet filter 28 to prevent or limit the amount of particulate matter passing from inner aspect 40 of inner container 22 through outlet 38.

A fluid may be supplied to inlet 36 by first passing through a conduit 42 coupled to a device for transporting a fluid. In one embodiment, the device for transporting a fluid may be a blower 44 used to transport a gas, such as, but not limited to, air, through conduit 42. A sensor 43, such as a flowmeter, may be coupled to conduit 42 for determining the rate of fluid flow into inner container 22.

Conduit 46 may be coupled to outlet 38 for receiving a fluid from inner container 22. Conduit 46 may also be coupled to a pressure sensor 48. Another conduit 50 may be coupled to inner container 22 at, for instance, and not by way of limitation, bottom end 34 and to pressure sensor 48. In this configuration, pressure sensor 48 may measure the pressure differential between top end 30 and bottom end 34 of inner container 22.

In at least one embodiment, a chamber 18, which may be referred to as an environmental chamber, may be coupled to test chamber 12 to control one or more parameters. Chamber 18 may be coupled to blower 44 and to conduit 46. Chamber 18 may be an apparatus for controlling parameters, such as, but not limited to, temperature, or humidity, or both. Chamber 18 may include sensors for determining the temperature and the humidity of a fluid in chamber 18. Chamber 18 may also be capable of controlling each parameter independently. In one embodiment chamber 18 is an oven with a refrigeration system. Valves 54 and 56 may be used to control inflow and outflow of fluids into and out of chamber 18.

Test chamber 12 may also include a load application device 58. Load application device 58 may be formed from a piston formed from a head 60 and a shaft 62. Shaft 62 may extend through top end 24 of outer container 20 and may be coupled to head 60. Top end 24 may include a seal for sealing top end 24 to shaft 62. In one embodiment, head 60 is configured to fit tightly in outer container 22. A seal, such as, but not limited to, a polytetraflouethylene seal, or an o-ring, maybe used to seal shaft 62 of load application device 58 to outer container 20. Load application device 58 may be coupled to any device capable of applying a force, or axial load, to shaft 62. The device may also include a gauge for determining and displaying the amount of force applied to load application device 58.

Particulate measuring system 10 may also include volume change sensor 14 for determining the volumetric change of inner container 22. Volume change sensor 14 may be coupled to test chamber 12 using conduit 64. Conduit 64 may be a conventional low pressure line or other conduit.

Volume change sensor 14 may also include a valve 66 for controlling air pressure and a calibration port 68 for calibrating the volume change sensor 14. Particulate measuring system 10 may also include a thermometer for determining the temperature of the air passed into the inner container 22, and a flowmeter from determining the amount of air passing into the inner container 22.

Volume change sensor 14 may also be coupled to computer 16. Computer 16 may be a conventional computer or other device capable of receiving analog data from volume change sensor 14 and converting the data to digital form, such as, but not limited to, a microcontroller or other such device. Computer 16 may be capable of displaying the results of data created by the particulate measuring system 10 in one or more formats. Computer 16 may also assemble two or more types of data and display the data in various formats.

The conduits described above may be any conduit capable of allowing a fluid to flow therethrough. The conduits may or may not be flexible and transparent. The conduits should be sized appropriately to handle the amount of fluid anticipated to flow through the conduits. In addition, the conduits may be composed of materials, such as, but not limited to, nylon, and plastics such as polyurethane, polypropylene, and others.

Figure 4:
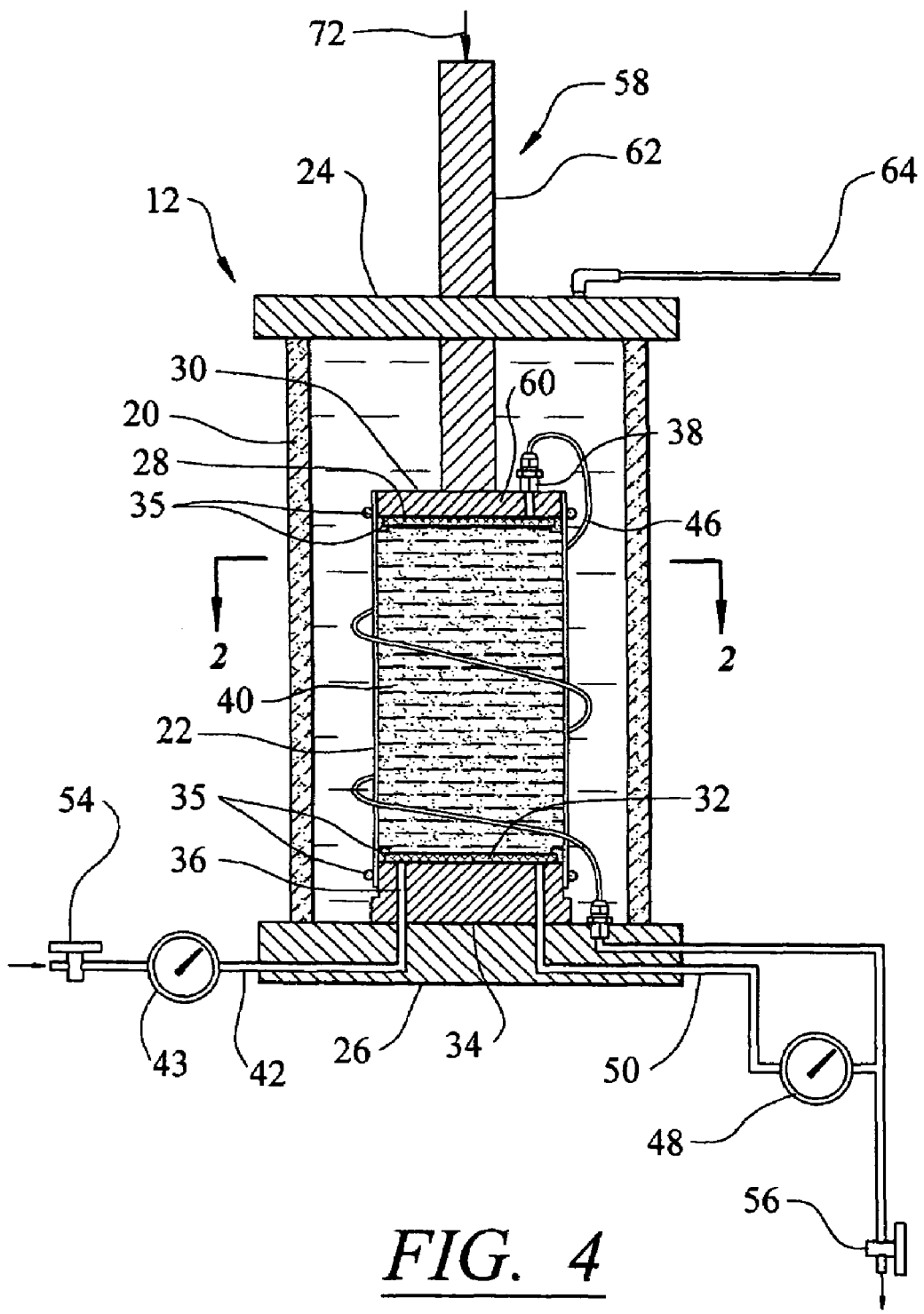
FIG. 4 is a schematic diagram of another embodiment of this invention including only the test chamber.
Figure 5:
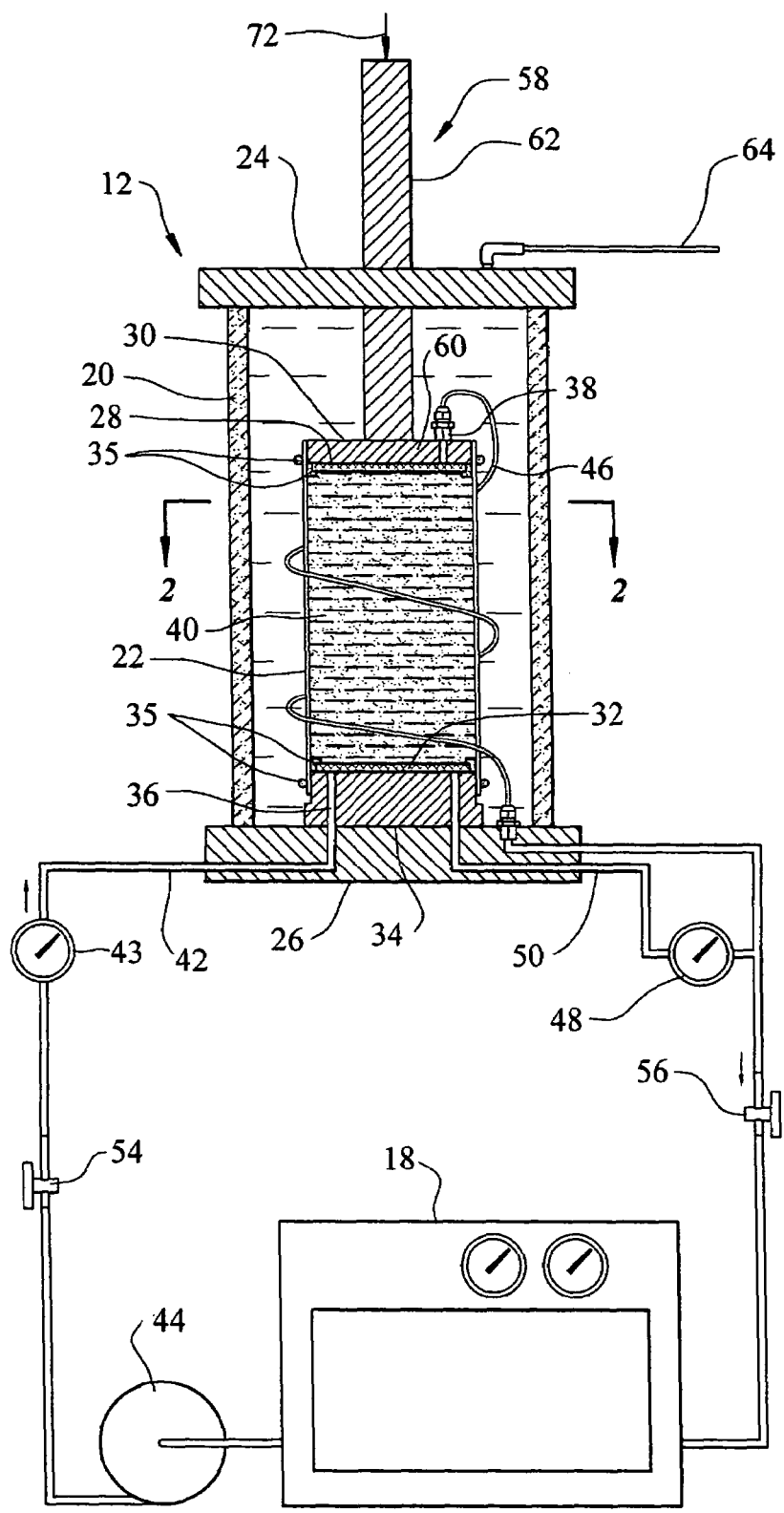
FIG. 5 is a schematic diagram of yet another embodiment of this invention including a test chamber and an environmental chamber.
Figure 6:
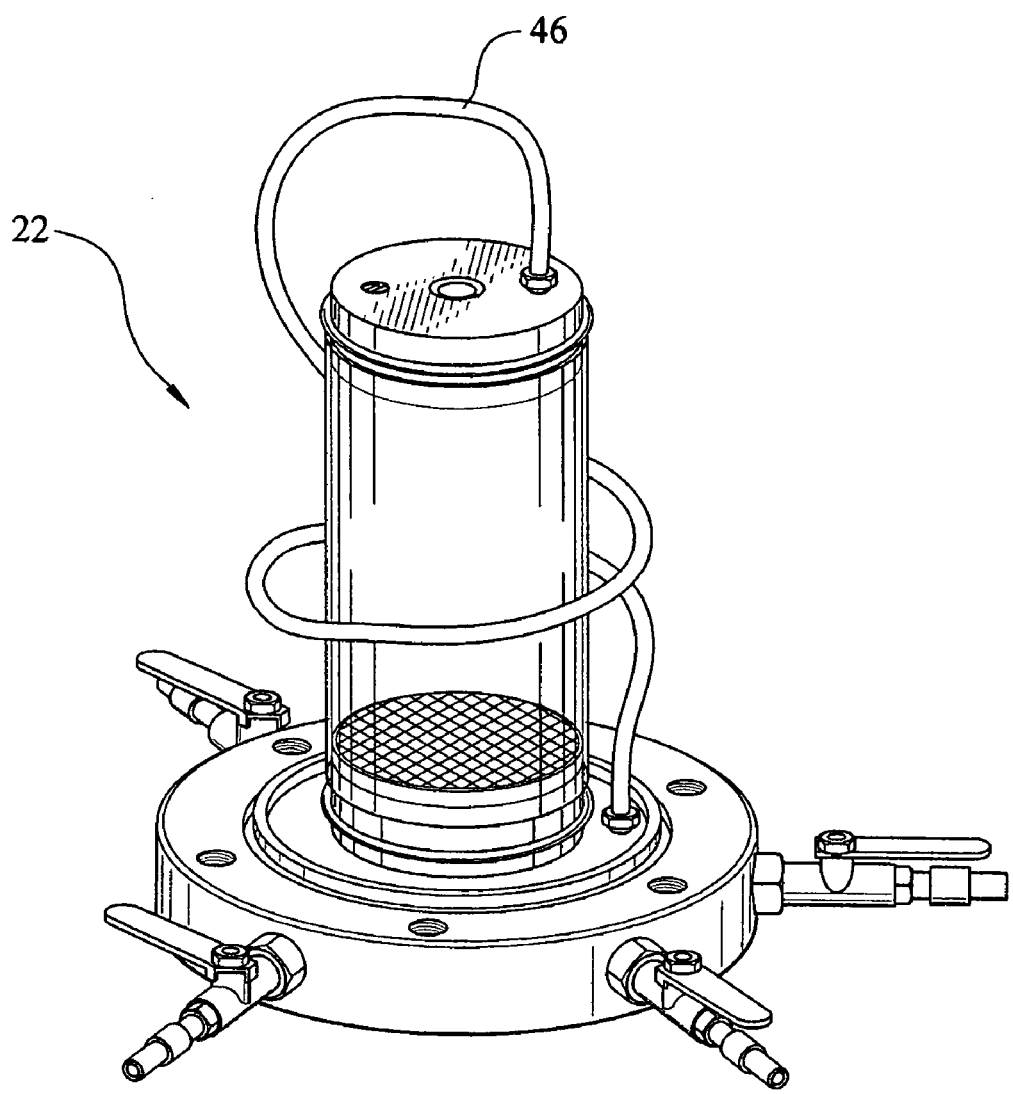
FIG. 6 is a perspective view of an inner chamber of the test chamber of this invention.

Particulate measuring system 10 may have one or more of the components previously described. As shown in FIG. 1, particulate measuring system 10 may include test chamber 12, volume change sensor 14 and computer 16. In another embodiment, as shown in FIG. 3, particulate measuring system 10 may also include environmental chamber 18. In yet another embodiment, as shown in FIG. 4, particulate measuring system 10 may consist only of test chamber 12. In still another embodiment, as shown in FIG. 5, particulate measuring system 10 may include test chamber 12 and environmental chamber 18. While these embodiments are shown as examples, these embodiments are not intended to limit the components that may form particulate measuring system 10.

Particulate measuring system 10 is configured to determine and quantify one or more characteristics of a particulate material. For instance and not by way of limitation, particulate measuring system 10 can determine the rate of gas flow through inner container 22, which in turn, may be used to determine the degree of aeration of the particulate material and whether the particulate material has reached a fluidized state. The rate of gas flow through the particulate measuring system 10 may be measured independently of other measurements that may be taken. Particulate measuring system 10 can also measure the pressure differential between bottom end 34 of inner container 22 and top end 30 of inner container 22, measure the total amount of axial load that a particulate material can be subjected to up to failure, where failure is the point at which a sample of particulate material fails to withstand any additional load, measure the pressure contained in outer container 20, and measure the volumetric change of inner container 22 using a volume change sensor 14 as an axial load is applied to a particulate material using load application device 58.

Particulate measuring system 10 is configured to receive a sample of a particulate material and determine parameters that may be used to design a handling system adequate to efficiently transfer the material during, for instance, a manufacturing process. Specifically, a particulate material may be placed in inner container 22. Inner container 22 may be sealed using, for instance, seal 35. Outer container 20 may then be filled with a fluid, such as, but not limited to, water. Preferably, an incompressible fluid or fluid that is incompressible at low pressures is used to fill outer container 20 so that the change in volume of inner container 22 may be accurately measured using volume change sensor 14. Alternatively, compressible fluids may be used such that the amount of compression of a fluid may be determined. The fluid in the space between the outer container 20 and the inner container 22 applies a confining pressure to the inner container 22.

Blower 44 may then be turned on to send a gas, such as air, through conduit 42 and inlet 36. The amount of gas entering particulate measuring system 10 may be controlled using valve 54. Upon leaving inlet 36, the gas may be distributed evenly into inner container 22 by passing the gas through inlet filter 32 at bottom end 34 of inner container 22. The gas then flows through the particulate material contained in inner container 22, through outlet filter 28 at top end 30 of inner container 22, through outlet 38, and into conduit 46. The gas then flows through conduit 46 and out of the system 10, or, in at least one embodiment, is returned to environmental chamber 18 where the temperature and humidity of the incoming air may be altered and controlled.

Particulate measuring system 10 may be capable of measuring the axial load strength of a particulate material with or without aeration. The axial load strength, specifically the load at which the particulate material fails, may be determined by applying a load in the direction of the arrow 72 in FIG. 1. While the axial load is being applied, volume change sensor 14 may determine the volumetric change of inner container 22, sensor 43 may determine the rate of flow of a gas through conduit 42, pressure sensor 48 may determine the pressure differential between the bottom end 34 of inner container 22 and top end 30 of inner container 22, and environmental chamber 18 may change the humidity and temperature of an incoming gas. Particulate measuring system 10 may control the following parameters individually, or two or more collectively: humidity, temperature, and gas flow through inner container 22. By changing each parameter individually, a more complete understanding of the effects of aeration on a particulate material may be acquired. In turn, a more efficient system may be constructed for handling and transporting the studied particulate material. The characteristics defined using particulate measuring system 10 may be used to develop constitutive equations defining a studied particulate material.

The foregoing is provided for purposes of illustrating, explaining, and describing embodiments of this invention. Modifications and adaptations to these embodiments will be apparent to those skilled in the art and may be made without departing from the scope or spirit of this invention.

We claim:

1. A device for measuring properties associated with aerated particles, comprising:
   an outer container adapted to contain a fluid;
   an inner container positioned in the outer container and having at least one inlet for admitting a gas and at least one outlet for releasing the gas; and
   at least one load application device passing through an outside wall of the outer container and forming an end of the inner container;
   wherein the fluid contained in the outer container is usable to determine changes in volume of aerated particles contained in the inner container.

2. The device of claim 1, wherein the inner container is formed from a membrane.

3. The device of claim 1, wherein the inner container is formed from latex.

4. The device of claim 1, further comprising at least one inlet filter for diffusing fluids entering the inner container and at least one outlet filter for substantially limiting particulate materials from being passed from the inner chamber.

5. The device of claim 1, further comprising at least one inlet coupled to a bottom portion of the inner container and at least one outlet coupled to a top portion of the inner container.

6. The device of claim 1, further comprising at least one blower in fluid communication with the at least one inner container.

7. The device of claim 1, further comprising a computer for recording data the device.

8. The device of claim 1, wherein the load application device is a piston formed from a head coupled to a shaft extending through the outer container.

9. The device of claim 1, further comprising at least one pressure sensing device coupled to the inner container.

10. The device of claim 1, further comprising a flowmeter for determining the rate of flow of air through the inner container, a thermometer for determining the temperature of the air flowing through the inner container, and a volume change sensor for determining the change in volume of the aerated particulate material in the inner chamber when a load is applied to the material.

11. The device of claim 1, further comprising an environmental chamber in fluid communication with the inner container for controlling environmental parameters selected from the group consisting of humidity and temperature.

12. The device of claim 6, wherein the environment chamber is selected from the group consisting of an oven and a refrigeration system.

13. A system for measuring properties associated with aerated particles, comprising:
   a chamber for containing a particulate material, comprising:
      an outer container for containing a fluid;
      an inner container positioned in the outer container and having at least one inlet and at least one outlet; and
      at least one load application device passing through an outside wall of the outer container and forming an end of the inner container;
   a volumetric change sensor for determining change in volume of the inner container by determining a change in level of the fluid in the outer container; and
   an storage device for storing parameters quantified using the chamber.

14. The system of claim 13, wherein the inner container is formed from a membrane.

15. The system of claim 13, wherein the inner container is formed from latex.

16. The system of claim 13, further comprising at least one inlet filter for diffusing fluids entering the inner container and at least one outlet filter for substantially limiting particulate materials from being passed from the inner chamber.

17. The system of claim 13, further comprising at least one inlet coupled to a bottom portion of the inner container and at least one outlet coupled to a top portion of the inner container.

18. The system of claim 13, wherein the storage device is a computer.

19. The system of claim 13, wherein the load application device is a piston formed from a head coupled to a shaft extending through the outer container.

20. The system of claim 13, further comprising at least one pressure sensing device coupled to the inner container.

21. The device of claim 13, further comprising a flowmeter for determining the rate of flow of air through the inner container, a thermometer for determining the temperature of the air flowing through the inner container, and a volume change sensor for determining the change in volume of the aerated particulate material in the inner chamber when a load is applied to the material.

22. The system of claim 13, further comprising an environmental chamber in fluid communication with the inner container for controlling environmental parameters selected from the group consisting of an oven and a refrigeration system.

23. The system of claim 22, wherein the environment chamber is adapted to control parameters selected from the group consisting of humidity and temperature.

24. A method for measuring properties associated with aerated particles, comprising:
   placing a sample of particulate material in a particulate measuring device, the particulate measuring device, comprising:
      an outer container for containing a fluid;
      an inner container containing the sample of particulate material, positioned in the outer container, and having at least one inlet and at least one outlet; and
      at least one load application device passing through an outside wall of the outer container and forming an end of the inner container;
      wherein the fluid contained in the outer container is usable to determine changes in volume of aerated particles contained in the inner container,
   filling the outer container with a fluid;
   aerating the particulate material by supplying air to the particulate material through the at least one inlet;
   applying a load to the particulate material using the at least one load application device; and
   determining the amount of load applied to the particulate material.

25. The method of claim 24, further comprising passing the air through at least one environmental chamber for controlling environmental parameters selected from the group consisting of humidity and temperature.

26. The method of claim 24, wherein determining the amount of load applied to the particulate material comprises using a storage device to record readings produced by devices selected from the group consisting of a pressure gauge, a thermometer, a flowmeter, and a volumetric sensor.

27. The method of claim 24, further comprising measuring the rate of gas flow through the particulate material contained in the inner container to determine the degree of aeration of the particulate material and whether the particulate material has reached a fluidized state.

28. The method of claim 24, further comprising measuring the pressure differential between the inlet and the outlet of the inner container, measuring the pressure contained in the outer container, and measuring the volumetric change of the inner container as an axial load is applied to a particulate material by measuring a change in fluid level in the outer container.

* * * * *